United States Patent [19]

Rezakhany

[11] 4,414,977
[45] Nov. 15, 1983

[54] NASAL DILATOR

[75] Inventor: Saeed Rezakhany, Madison, Wis.

[73] Assignee: Wisconsin Alumni Research Foundation, Madison, Wis.

[21] Appl. No.: 284,654

[22] Filed: Jul. 20, 1981

[51] Int. Cl.³ .................. A61M 29/00; A61F 5/08
[52] U.S. Cl. ................................ 128/342; 128/341; 128/76 C
[58] Field of Search ............... 128/341, 342, 343, 20, 128/130, 76 C

[56] References Cited

U.S. PATENT DOCUMENTS

| | | |
|---|---|---|
| 1,597,331 | 8/1926 | Thurston et al. |
| 1,672,591 | 6/1928 | Wells .................. 128/342 |
| 1,709,740 | 4/1929 | Rogers ................ 128/342 |
| 2,335,936 | 12/1943 | Hanlon . |
| 2,672,138 | 3/1954 | Carlock . |
| 3,192,928 | 7/1965 | Horton . |
| 3,710,799 | 1/1973 | Caballero ............ 128/342 |
| 4,105,035 | 8/1978 | Rella . |

FOREIGN PATENT DOCUMENTS 270724 3/1913 Fed. Rep. of Germany .
469010 7/1914 France .

*Primary Examiner*—Kyle L. Howell
*Assistant Examiner*—C. W. Shedd
*Attorney, Agent, or Firm*—Isaksen, Lathrop, Esch, Hart & Clark

[57] ABSTRACT

A nasal dilator (10) is disclosed which is adapted to be inserted in the nostril of the human nose to prevent the tissues of the ostium internum of the nose from drawing in during breathing. The device includes generally elongated top and bottom rings (11, 12) which are spaced apart and connected together by a rear strut (13) and a front strut (14). The front strut (14) is longer than the rear strut (13) and includes a bend (15) therein formed at a position close to the front end of the bottom ring (12). One elongated side (17) of the top ring (11) may be concaved to better fit the septum at the ostium internum, and an elongated side (18) of the bottom ring (12) may also be concaved for maximum wearer comfort. When emplaced in the nose, the top ring (11) fits comfortably in the ostium (31) within the nostril to prevent the tissues therein from being drawn in during inhalation and to reduce extra flow resistance during exhalation, and the bottom ring (12) fits above the entrance to the nostril and serves to stabilize the position of the top ring within the nostril.

6 Claims, 6 Drawing Figures

NASAL DILATOR

TECHNICAL FIELD

This invention relates generally to the field of medical and surgical devices utilized to aid breathing through the nose in certain patients having normally blocked nasal passages.

BACKGROUND ART

A large proportion of the human population has some misformation of the nasal passages which makes breathing difficult, such as a deviated septum—the dividing wall between the two nasal passages. The lower portion of the nostril, immediately above the entrance to the nostril, is known as the vestibule, and is a structure which tapers inwardly to a narrowed neck-like area called the ostium internum. Above the ostium internum the nasal passages widen out again. Nasal obstructions commonly occur at the ostium in individuals who have a deviated septum and similar conditions, to the point that the ostium may be substantially blocked. Commonly, the lateral wall of the vestibule at the ostium is loose, with the result that the wall draws in during the process of inhalation to substantially block passage of air through the ostium. The loose skin tissues may act as a "check-valve" in that they draw in to block air flow during in-breathing, but may open up again to allow air to be exhaled.

Blockage of the nasal passages is obviously an inconvenience to persons who experience it, but it may ultimately result in more serious problems. In particular, sustained mouth breathing over a long period of time can lead to a variety of chronic problems including malformation of the teeth, sleep disturbances because of irregularity of breathing, and possible lung irritation from mouth breathing in cold weather and from breathing in foreign particles that would otherwise be filtered if the breath had been passed through the nose.

The most common approach to a serious and chronic nasal blockage problem as described above is a surgical attempt to correct the malformation of the nasal passages. However, surgery is not only expensive, time consuming, and somewhat unpleasant and dangerous, in many cases surgery fails to correct the problem. A number of nasal dilation devices have been devised in an attempt to provide an alternative to surgery in correcting the problem of blocked nasal passages. Typically, these devices have provided a forced dilation or separation of the nasal tissues to open up the passages, such as is shown in U.S. Pat. Nos. 1,597,331; 2,335,936; 2,672,138; and 4,105,035. Some of these devices attempt to physically distort the bone and cartilage as well as the soft tissue of the nostril in order to provide a wider passage. However, such devices have apparently not found favor, perhaps because of ineffectiveness, discomfort in wearing, difficulty of insertion, expense or other factors.

DESCRIPTION OF THE INVENTION

The nasal dilator of the present invention is a simple, inexpensive and easily used device which addresses itself to the problem of blocked nose breathing caused by an excessively narrow nasal vestibule combined with loose lateral wall tissue at the ostium which normally draws in during breathing to substantially or completely block the passage. In accordance with the invention, it is found that radical dilation or restraint of the nasal tissues is not necessary to cure the problem of nasal tissue being drawn in to block breathing, and the device of the invention provides a minimal structure which restrains the tissues of the nose without deforming them to the point of causing discomfort. It is easily inserted and removed by the wearer, invisible when worn, and is so comfortable to the wearer that it can be used over long periods of time without removal.

The device of the invention includes a pair of ring members each having a generally elongated oval shape. The bottom ring member is somewhat larger than the top ring member and is spaced away therefrom by a pair of struts, the rear strut being substantially straight and connected between the rear ends of the top and bottom ring members, and the front strut being substantially longer, connected between the front ends of the top and bottom rings, and having a bend spaced closer to the bottom ring member and formed such that the front strut engages the bottom ring at an angle substantially perpendicular to the plane of the bottom ring. The top and bottom rings are preferably slightly dimpled or concaved along one of their elongated sides to adapt the device for insertion in either the right or left nostril, depending on which side of the ring members the concavity is formed.

The spacing between the top and bottom ring members is selected such that when the bottom ring member is above the entrance to the nostril, the top ring will be at approximately the ostium internum portion of the nasal passage. The top ring engages the walls of the ostium to hold back or retain the tissues therein to prevent them from being drawn in during in-breathing. The bottom ring sits above the entrance to the nostril. The larger bottom ring prevents the device from being drawn up in the nose during breathing. The device is held within the nostril primarily by the minor pressure exerted by the lateral vestibule wall and local drying of nasal secretions in the vestibule.

The bend formed in the front strut adapts to the shape of the front of the nostril, allowing the strut to be more firmly and comfortably engaged within the nose, and the front strut extends upwardly to connection with the top ring such that the top ring is disposed at an angle with respect to the bottom ring which is selected such that the top ring is positioned approximately parallel to the plane of the ostium. In this manner, the top ring is in the most ideal position to hold open the ostium without stressing the surrounding tissues. Only light engagement between the top ring and the tissues of the nose is required to achieve the effect of preventing these tissues from being drawn in during inhalation, thus minimizing any discomfort on the part of the wearer.

The materials of the rings and struts are biocompatible, such as stainless steel or polyurthane, and do not irritate the tissue lining. The diameter of the material forming the rings and struts is preferably made as small as possible to minimize interference with the flow of air through the nose; the only limit on the smallness of these structures is imposed by the mechanical strength required and the need to avoid creating sharp edges and other points of undue stress on the tissue of the nose which might cut the tissue or at least irritate it. The overall sizes and angles of the rings and struts can be selected to conform to the sizes and shapes of nasal passages occuring in various individuals, in much the same manner as contact lenses are shaped and sized, so that each wearer is assured of the maximum individual comfort and effectiveness.

Further objects, features, and advantages of the invention will be apparent from the following detailed description taken in conjunction with the drawings showing preferred embodiments of a nasal dilator in accordance with the invention.

BEST MODE FOR CARRYING OUT THE INVENTION

Figure 1:
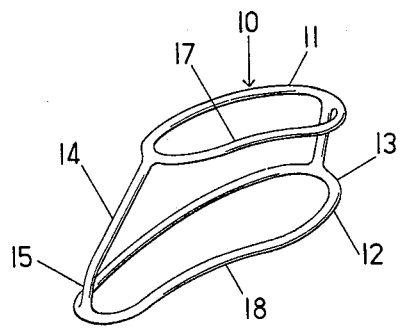
FIG. 1 is a perspective view of a nasal dilator in accordance with the invention which is intended for use in the right nostril of an individual.
Figure 2:
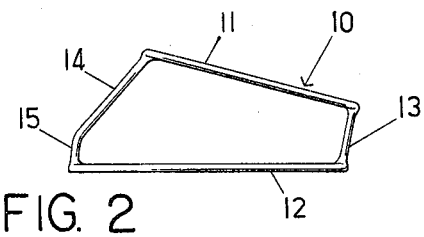
FIG. 2 is a side elevation view of the dilator of FIG. 1.

With reference to the drawings, a preferred embodiment of a nasal dilator in accordance with the invention is shown generally at 10 in FIGS. 1-4. The dilator 10 has a top ring member 11 and a bottom ring member 12 and a rear strut 13 and a front strut 14 which connect the ring members together in spaced relation. The ring members are of an elongated oval shape, with the bottom ring member being longer than the top ring member in the elongated dimension of the ring members. The rear strut 13 is connected to the ring members at the rear ends thereof, while the front strut 14 is connected to the ring members at the front ends thereof. The front strut 14 has a bend 15 formed therein at a point spaced closer to the bottom ring member 12 than to the top ring member 11, and the form of the bend 15 is such that the strut 14 engages the ring member 12 at an angle approximately perpendicular to the plane of the bottom ring member.

Figure 3:
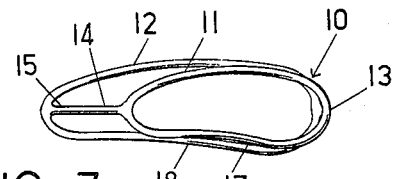
FIG. 3 is a top view of the dilator of FIG. 1.
Figure 4:
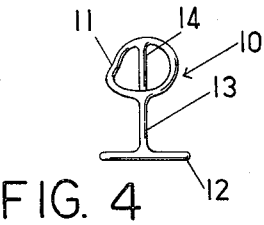
FIG. 4 is a rear elevation view of the prosthesis of FIG. 1.

As best shown in the views of FIGS. 1 and 3, the top ring member 11 has a concavity or dimple 17 formed along one elongated side of the ring member while the bottom ring member 12 also has a concavity or dimple 18 formed in one elongated side, the two concavities 17 and 18 being adjacent to one another. This concavity in the top and bottom ring members adapts the dilator for insertion into the right nostril of an individual, since the concavities 17 and 18 generally conform, respectively, to the bulging out of the septum at the ostium and to the raised cartilage and tissue at the entrance of the nostril. In some individuals, the septum does not show a significant bulge, and therefore no concavity need be formed in the elongated side of the top ring member. The concavity in the elongated side of the lower ring is preferred for maximum comfort but is not critical to the performance of the device.

Figure 6:
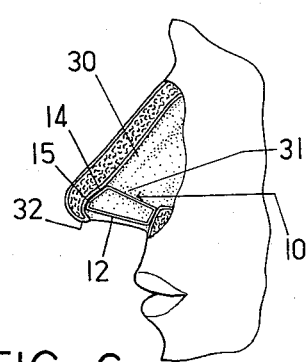
FIG. 6 is an illustrative view showing the nasal dilator of the invention emplaced within the nose of a wearer shown partially in cross-section.

The dilator 10 is shown emplaced illustratively in the nostril 30 of an individual in FIG. 6. As shown therein, the top ring member 11 is positioned to be substantially at the ostium 31 of the vestibule within the nostril so that it is in substantial and firm, although not stressful, engagement with the tissues of the nostril at this point. Engagement of the top ring 11 with the walls of the ostium prevents the surrounding tissue from being drawn in and cutting off the flow of air therethrough. The bottom ring 12 is positioned to fit above the entrance to the nostril at a point just above the lip 32 found in the nostril of each normal individual. It can be seen from an examination of FIG. 6 that the bend 15 formed in the front strut 14 enables the strut to comfortably contact the front surface of the interior of the nostril near the juncture with the bottom ring 12, and to continue this engagement between front strut and front of the nostril up to the joint between the strut and the top ring 11. The engagement between the front strut and the front surface of the interior of the nostril prevents the dilator 12 from flopping or wiggling around within the nostril which might otherwise occur.

Figure 5:
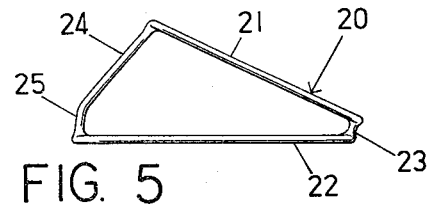
FIG. 5 is a side elevation view of a varied embodiment of the nasal dilator of the invention which has a shortened rear strut.

It is found that the shape and size of the human nostril varies between individuals. For example, the angle at which the nostril extends back from the entrance to the nostril may be more acute than is shown in FIG. 6. For such a case, preferred fitting of the dilator within the nostril of the individual requires that the top and bottom rings be disposed at a more acute angle to one another than is shown for the prosthesis 10 of FIGS. 1-4. A modified embodiment of the dilator which is adapted to such a situation is shown generally at 20 in FIG. 5. This dilator also has a top ring 21, a bottom ring 22, a rear strut 23, and a front strut 24 with a bend 25 in it, each of these structures being substantially identical in shape, material, and function to the corresponding structures of the embodiment 10 shown in FIGS. 1-4. However, the rear strut 23 is formed much shorter than the rear strut 13, thereby resulting in a more acute angle between the top ring 21 and the bottom ring 22. It is quite apparent that the shape and sizing of the struts, as well as the rings themselves, may be selected to adapt the dilator to the needs of the individual.

Since human nostrils vary widely in size and shape, it may be necessary, for particular individuals, to adjust the device such that the top ring is disposed at a sideways angle to the bottom ring to accomodate deviations in the nasal passage. The device may be so customized by twisting the top ring sideways in the desired direction if the materials of the device allow such plastic deformation without damage.

Typical dimensions for the components of the dilator of the invention would include the length of the top ring in the elongated dimension of approximately one-half inch and approximately one-quarter inch in width, with the bottom ring being aapproximately the same width and one and one-half times as long as the top ring, or generally three-quarters to one inch in length. The distance between the front ends of the top and bottom rings will typically be in the range of one-half to five-eighths inch, whereas the distance between the rear ends of the top and bottom rings will typically be in the range of one-quarter inch or less. The material forming the top and bottom rings and the struts is preferably made as thin as possible to minimize the interference of the structure with free flow of air through the nostril, and a typical construction utilizes material having a circular cross-section and a diameter of one-thirty-second inch or less. The minimum diameter of these structures is selected to provide sufficient structural strength and to avoid sharp edges or corners which could cause undue stress on body tissues or even cut the tissues. Materials having a cross-sectional dimension of approximately one-thirty-second inch have been found satisfactory. Wire having a ribbon shape or an elliptical cross-section may also be used. The materials of which the rings and struts are made are biocompatible, such as stainless steel and polyurthane. The rings and struts may be formed of stainless steel wire, with the ends of the wire forming the rings being attached together with cadmium free silver solder and with the struts similarly being attached to the rings with cadmium free silver solder. With the use of a wire structure of this nature, the spacing between the top and bottom rings may be varied by bending the struts to lessen the distance between the rings, particularly by bending the rear strut 13 inwardly to reduce the spacing between the rear ends of the top and bottom rings. Although it is preferred that the dilator be custom fitted to each individual, it is apparent that a single model of the dilator may be adapted to fit the nostrils of several individuals.

While specific embodiments of the invention have been shown and described herein, it is understood that the invention is not so limited, and the invention embraces such modified forms thereof as come within the scope of the following claims.

I claim:

1. A nasal dilator adapted for emplacement in the vestibule of the nose to retain the tissues therein and provide a free air passage, comprising:
   (a) a top ring member having a generally elongated oval shape;
   (b) a bottom ring member having a generally elongated oval shape and being longer in the elongated dimension than the top ring;
   (c) a substantially straight rear strut extending between the rear elongated ends of the top and bottom ring members;
   (d) a front strut extending between the front elongated ends of the top and bottom ring members, the front strut being substantially longer than the rear strut and having a bend therein spaced closer to the bottom ring than to the top ring and arranged such that the front strut engages the bottom ring approximately perpendicular to the plane of the bottom ring, the top ring being sized to extend approximately the length of the ostium internum of the human nose, the bottom ring being sized to extend approximately the length of the bottom of the vestibule adjacent to the opening of the nostril, the struts spacing the top ring from the bottom ring a distance approximately equal to the distance from the ostium internum of the nostril to the bottom thereof, the top and bottom rings and the struts being formed of a non-irritating, biocompatible material.

2. The dilator of claim 1 wherein one of the elongated sides of the top ring is concaved inwardly to adapt the top ring to fit firmly but without undue pressure to the ostium internum of the human nose with the concave side of the ring being adjacent to the inner or septum side of the nostril so that the dilator is adapted to be worn inside either the left or right nostril of the nose depending on which side of the ring the concavity is formed.

3. The dilator of claim 2 wherein the elongated side of the bottom ring which is adjacent to the concaved side of the top ring is also concaved.

4. The dilator of claim 1 wherein the top and bottom rings and the struts are formed of stainless steel wire, wherein the ends of the wires forming the rings are attached together with cadmium free silver solder, and wherein the struts are attached to the top and bottom rings with cadmium free silver solder.

5. The dilator of claim 1 wherein the top ring is approximately one-half inch in the long dimension and the bottom ring is approximately three-quarters inch in the long dimension, and wherein the material forming the rings and the struts is circular in cross-section and about one-thirty-second inch in diameter.

6. The dilator of claim 1 wherein the front ends of the top and bottom rings are spaced approximately five-eighths inch apart and the rear ends of the top and bottom rings are spaced approximately one-quarter inch apart.

* * * * *